US00PP25394P2

(12) United States Plant Patent
Tsutsumi

(10) Patent No.: US PP25,394 P2
(45) Date of Patent: Mar. 31, 2015

(54) *VERBENA* PLANT NAMED 'RIKAV17805'

(50) Latin Name: *Verbena hybrida*
Varietal Denomination: RIKAV17805

(71) Applicant: Rika Tsutsumi, Higashiomi (JP)

(72) Inventor: Rika Tsutsumi, Higashiomi (JP)

(73) Assignee: Plant 21 LLC, Bonsall, CA (US)

( * ) Notice: Subject to any disclaimer, the term of this patent is extended or adjusted under 35 U.S.C. 154(b) by 130 days.

(21) Appl. No.: 13/815,877

(22) Filed: Mar. 15, 2013

(51) Int. Cl.
*A01H 5/00* (2006.01)

(52) U.S. Cl.
USPC ..... Plt./308

(58) Field of Classification Search
CPC ..... A01H 5/02; A01H 5/00
USPC ..... Plt./308
See application file for complete search history.

*Primary Examiner* — June Hwu
(74) *Attorney, Agent, or Firm* — C. A. Whealy

(57) ABSTRACT

A new and distinct cultivar of *Verbena* plant named 'RIKAV17805', characterized by its compact, outwardly spreading and mounding plant habit; vigorous growth habit; freely branching habit; dark green-colored leaves; freely flowering habit; white-colored flowers that are held above and beyond the foliar plane; and relative tolerance to powdery mildew.

1 Drawing Sheet

Botanical designation: *Verbena hybrida.*
Cultivar denomination: 'RIKAV17805'.

BACKGROUND OF THE INVENTION

The present invention relates to a new and distinct cultivar of *Verbena* plant, botanically known as *Verbena hybrida*, and hereinafter referred to by the name 'RIKAV17805'.

The new *Verbena* plant is a product of a planned breeding program conducted by the Inventor in Higashiomi, Shiga, Japan and Bonsall, Calif. The objective of the breeding program is to create new vigorous and freely-branching *Verbena* plants with numerous flowers and tolerance to powdery mildew.

The new *Verbena* plant originated from a cross-pollination made by the Inventor on May 5, 2010 in Higashiomi, Shiga, Japan of a proprietary seedling selection of *Verbena hybrida* identified as code number 08V603-01, not patented, as the female, or seed, parent with a proprietary seedling selection of *Verbena hybrida* identified as code number 09V852-01, not patented, as the male, or pollen, parent. The new *Verbena* plant was discovered and selected by the Inventor as a single flowering plant from within the progeny of the stated cross-pollination in a controlled greenhouse environment in Bonsall, Calif. on Jun. 9, 2011.

Asexual reproduction of the new *Verbena* plant by terminal cuttings in a controlled environment in Bonsall, Calif. since Jun. 10, 2011 has shown that the unique features of this new *Verbena* plant are stable and reproduced true to type in successive generations.

SUMMARY OF THE INVENTION

Plants of the new *Verbena* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'RIKAV17805'. These characteristics in combination distinguish 'RIKAV17805' as a new and distinct *Verbena* plant:

1. Compact, outwardly spreading and mounding plant habit.
2. Vigorous growth habit.
3. Freely branching habit.
4. Dark green-colored leaves.
5. Freely flowering habit.
6. White-colored flowers that are held above and beyond the foliar plane.
7. Relatively tolerant to powdery mildew.

Plants of the new *Verbena* can be compared to plants of the female parent selection. Plants of the new *Verbena* differ primarily from plants of the female parent selection in the following characteristics:

1. Plants of the new *Verbena* are more freely branching than plants of the female parent selection.
2. Leaves of plants of the new *Verbena* are darker green in color than leaves of plants of the female parent selection.

Plants of the new *Verbena* can be compared to plants of the male parent selection. Plants of the new *Verbena* differ primarily from plants of the male parent selection in the following characteristics:

1. Plants of the new *Verbena* are more mounding than and not as upright as plants of the male parent selection.
2. Plants of the new *Verbena* are more freely flowering than plants of the male parent selection.

Plants of the new *Verbena* can be compared to plants of the *Verbena hybrida* 'AKIV344-01', disclosed in U.S. Plant Pat. No. 21,643. In side-by-side comparisons conducted in Bonsall, Calif., plants of the new *Verbena* differed primarily from plants of 'AKIV344-01' in the following characteristics:

1. Plants of the new *Verbena* were more compact and mounding than and not as trailing as plants of 'AKIV344-01'.
2. Leaves of plants of the new *Verbena* were darker green in color than leaves of plants of 'AKIV344-01'.

3. Plants of the new *Verbena* and 'AKIV344-01' differ in flower color as plants of 'AKIV344-01' have pink-colored flowers.

Plants of the new *Verbena* can also be compared to plants of the *Verbena hybrida* 'Vepita White', not patented. In side-by-side comparisons conducted in Bonsall, Calif., plants of the new *Verbena* differed primarily from plants of 'Vepita White' in the following characteristics:

1. Plants of the new *Verbena* were larger than plants of 'Vepita White'.
2. Plants of the new *Verbena* had larger flowers than plants of 'Vepita White'.
3. Plants of the new *Verbena* were more tolerant to powdery mildew than plants of 'Vepita White'.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the actual colors of the new *Verbena* plant.

The photograph at the bottom of the sheet comprises a side perspective view of a typical flowering plant of 'RIKAV17805' grown in a container.

The photograph at the top of the sheet is a close-up view of a typical flowering plant of 'RIKAV17805'.

DETAILED BOTANICAL DESCRIPTION

The aforementioned photographs and following observations, measurements and values describe plants grown during the late autumn in 11.4-cm containers in a polyethylene-covered greenhouse in Bonsall, Calif. During the production of the plants, day temperatures ranged from 21° C. to 38° C., night temperatures averaged 21° C. and light levels ranged from 7,000 to 10,000 foot-candles. Plants were pinched one time at planting and were two months old when the photographs and description were taken. In the following description, color references are made to The Royal Horticultural Society Colour Chart, 2007 Edition, except where general terms of ordinary dictionary significance are used.

Botanical classification: *Verbena hybrida* 'RIKAV17805'.

Parentage:

*Female, or seed, parent*.—Proprietary seedling selection of *Verbena hybrida* identified as code number 08V603-01, not patented.

*Male, or pollen, parent*.—Proprietary seedling selection of *Verbena hybrida* identified as code number 09V852-01, not patented.

Propagation:

*Type cutting*.—Vegetative tip cuttings.

*Time to initiate roots, summer*.—About three days at temperatures ranging from about 16° C. to 29° C.

*Time to initiate roots, winter*.—About four days at temperatures ranging from about 16° C. to 21° C.

*Time to produce a rooted plant, summer*.—About 15 days at temperatures ranging from about 16° C. to 29° C.

*Time to produce a rooted plant, winter*.—About 20 days at temperatures ranging from about 16° C. to 21° C.

*Root description*.—Medium in thickness, fibrous; white in color.

*Rooting habit*.—Freely branching; medium density.

Plant description:

*Plant and growth habit*.—Compact, outwardly spreading and mounding plant habit; freely branching habit with about five to six primary lateral branches developing per plant each with numerous secondary branches; pinching enhances lateral branch development; dense and bushy plant habit; vigorous growth habit.

*Plant height*.—About 19.5 cm.

*Plant diameter* (*spread*).—About 37 cm by 41 cm.

Lateral branch description:

*Length*.—About 21 cm.

*Diameter*.—About 2.5 mm.

*Internode length*.—About 2.7 cm.

*Orientation*.—Initially upright then outwardly spreading and decumbent.

*Strength*.—Strong.

*Texture*.—Pubescent; minute.

*Color*.—Close to 147B.

Leaf description:

*Arrangement*.—Opposite, simple.

*Length*.—About 7.4 cm.

*Width*.—About 4.1 cm.

*Shape*.—Oblong to ovate.

*Apex*.—Broadly acute.

*Base*.—Attenuate.

*Margin*.—Broadly crenate.

*Texture, upper and lower surfaces*.—Pubescent; coarse, hirsute.

*Venation pattern*.—Pinnate; reticulate.

*Color*.—Developing leaves, upper surface: Close to 137B. Developing leaves, lower surface: Close to 146B. Fully expanded leaves, upper surface: Close to 147A; venation, close to 147B. Fully expanded leaves, lower surface: Close to 147B; venation, close to 148C.

*Petiole*.—Length: About 1 cm. Diameter: About 3 mm. Texture, upper and lower surfaces: Densely pubescent. Color, upper and lower surfaces: Close to 146C.

Flower description:

*Flower arrangement and habit*.—Sessile salverform flowers arranged in compact hemispherical terminal racemes; flowers face upward or outwardly; freely flowering habit with about 44 flowers developing per inflorescence and typically more than 400 flowers per plant.

*Natural flowering season*.—Plants flower continuously from spring through the autumn in southern California; early flowering habit, plants begin flowering about five weeks after planting.

*Flower longevity*.—Flowers last about five to seven days on the plant; flowers not persistent.

*Fragrance*.—None detected.

*Inflorescence height*.—About 4.4 cm.

*Inflorescence diameter*.—About 5.5 cm.

*Flower buds*.—Length: About 2.1 cm. Diameter: About 3 mm. Shape: Elongated oblong. Color: Close to 155A.

*Flower diameter*.—About 1.6 cm.

*Flower depth* (*height*).—About 2.7 cm.

*Throat diameter*.—About 1.5 mm.

*Tube length*.—About 2 cm.

*Tube diameter, proximal*.—About 1.5 mm.

*Corolla*.—Arrangement: Single whorl of five fused petals fused towards the base into a narrow tube. Petal lobe length: About 7 mm. Petal lobe width: About 6 mm. Petal lobe shape: Roughly cordate. Petal lobe apex: Emarginate to cordate. Petal margin: Entire. Petal texture, upper and lower surfaces: Smooth, glabrous; velvety. Throat texture: Smooth, glabrous. Tube texture: Sparsely pubescent. Color: Petal, when opening, upper and lower surfaces: Close to NN155D. Petal, fully opened, upper and lower surfaces: Close to NN155D; color does not change with development. Throat: Close to 157D; distally, small ring, close to 145A. Tube: Close to 157B.

*Calyx*.—Arrangement: Single whorl of five fused sepals fused towards the base into a slender tube. Sepal length: About 1.4 cm. Sepal width: About 1 mm. Sepal shape: Narrowly lanceolate. Sepal apex: Acute. Sepal margin: Entire. Sepal texture, inner surface: Smooth, glabrous. Sepal texture, outer surface: Pubescent; minute. Sepal color, upper surface: Close to 144D. Sepal color, lower surface: Close to 146B.

*Peduncles*.—Length: About 2.2 cm. Diameter: About 2 mm. Strength: Strong. Texture: Pubescent. Color: Close to 146B.

*Reproductive organs*.—Stamens: Quantity and arrangement: Four per flower, filaments are adnate to corolla tube. Filament length, free section: About 1 mm. Filament color: Close to 145C. Anther shape: Oval. Anther length: About 1 mm. Anther color: Close to 151A. Pollen amount: Scarce. Pollen color: Close to N144D. Pistils: Quantity: One per flower. Pistil length: About 1.9 cm. Stigma shape: Rounded, biparted. Stigma color: Close to 144A. Style length: About 1.5 cm. Style color: Close to 145D. Ovary color: Close to 144A. Fruits and seeds: Fruit and seed development have not been observed on plants of the new *Verbena*.

Temperature tolerance: Plants of the new *Verbena* have been observed to tolerate temperatures from about 1° C. to about 40° C.

Pathogen & pest resistance: Plants of the new *Verbena* have been observed to be relatively tolerant to powdery mildew. Plants of the new *Verbena* have not been observed to be resistant to pests and other pathogens common to *Verbena* plants.

It is claimed:

1. A new and distinct *Verbena* plant named 'RIKAV17805' as illustrated and described.

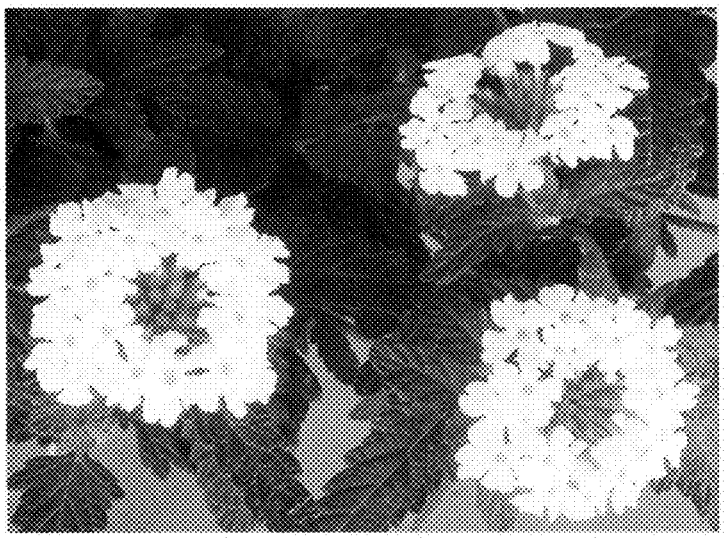
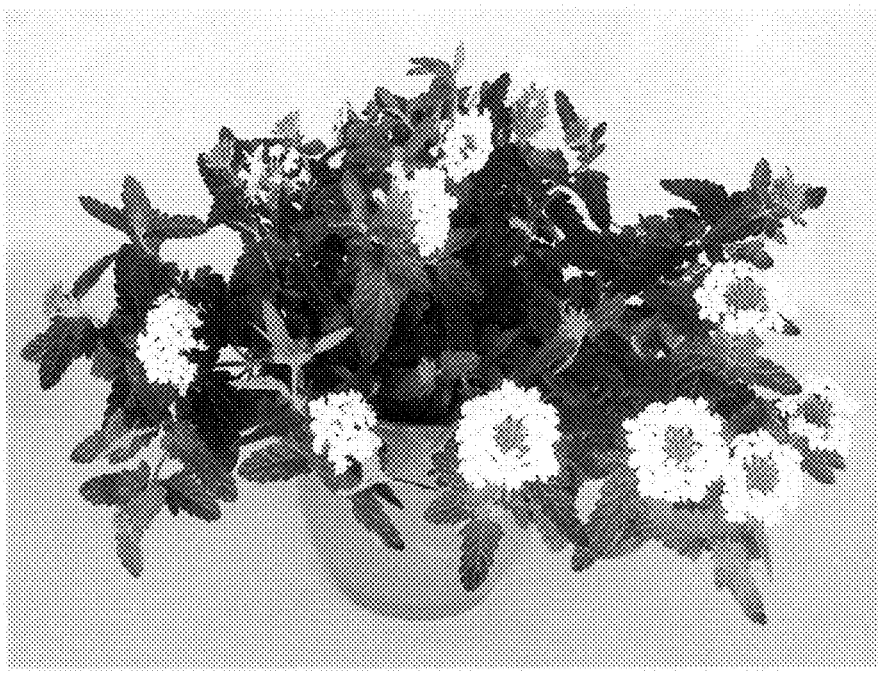

* * * * *